(12) United States Patent
Palm

(10) Patent No.: US 7,127,302 B2
(45) Date of Patent: Oct. 24, 2006

(54) ELECTRODE LEAD

(75) Inventor: Jochen Palm, Mahlow (DE)

(73) Assignee: Biotronik GmbH & Co. KG (DE)

( * ) Notice: Subject to any disclaimer, the term of this patent is extended or adjusted under 35 U.S.C. 154(b) by 90 days.

(21) Appl. No.: 10/958,892

(22) Filed: Oct. 5, 2004

(65) Prior Publication Data
US 2006/0074471 A1    Apr. 6, 2006

(51) Int. Cl.
*A61N 1/05*    (2006.01)
(52) U.S. Cl. .............. 607/119; 607/120; 607/127; 600/375
(58) Field of Classification Search ........ 607/116–129; 600/373–381
See application file for complete search history.

(56) References Cited
U.S. PATENT DOCUMENTS

| | | | |
|---|---|---|---|
| 6,192,280 B1 | 2/2001 | Summer et al. | |
| 6,363,288 B1 * | 3/2002 | Bush et al. | 607/122 |
| 6,567,704 B1 * | 5/2003 | Sundquist et al. | 607/119 |
| 6,931,286 B1 * | 8/2005 | Sigg et al. | 607/120 |

\* cited by examiner

*Primary Examiner*—Mark Bockelman
(74) *Attorney, Agent, or Firm*—Hahn Loeser & Parks, LLP; John J. Cunniff

(57) ABSTRACT

An intracardial electrode lead comprises a distal end, a proximal end and an elongate electrode lead body which includes a helical coil having a lumen and a sheath enclosing the helical coil. The distal end of the electrode lead carries a an electrode. The electrode is electrically connected to a connection at the proximal end of the electrode lead for communication with a medical device. The distal end has a sleeve with a proximal end and a distal end, which is enclosed by the distal end of the helical coil at the sleeve proximal end and contacts a lip seal at its distal end. The lip seal elastically closes a distal opening of the lumen. The sleeve is also electrically connected to the electrode, which has an external surface and projects distally beyond the lip seal.

20 Claims, 4 Drawing Sheets a)

b)

c)

d)

ELECTRODE LEAD

BACKGROUND OF THE INVENTION

The invention concerns an intracardial electrode lead, which, as its name indicates, is suitable for arrangement in a heart, in particular in a human heart. The electrode lead is adapted for connection to a cardiac therapy device such as a cardiac pacemaker, defibrillator or cardioverter. The assembly includes an elongate electrode lead body which has a longitudinally extending helical coil with a lumen for a guide wire or the like. The helical coil is surrounded by an insulating and sealing sheath. The electrode lead has a distal end and a proximal end, and in the region of its distal end, carries a stimulation and/or sensing electrode which is electrically connected to a connection at the proximal end of the electrode lead.

Electrode leads of this kind are basically known in various different variations. In the patent literature, electrode leads of that kind are described for example in WO 00/72911.

The object of the invention is to provide an electrode lead which is optimized in regard to various properties.

SUMMARY OF INVENTION

According to the invention, that object is attained by an electrode lead comprising a distal end, a proximal end and an elongate electrode lead body. The electrode lead body includes a helical coil having a lumen and a sheath enclosing the helical coil. The distal end of the electrode lead carries a stimulation electrode, a sensing electrode or both. The electrode is electrically connected to a connector at the proximal end of the electrode lead for communication with a medical device. The distal end of the electrode line has a sleeve with a proximal end and a distal end. The proximal end of the sleeve is enclosed by the distal end of the helical coil. The distal end of the sleeve contacts a lip seal. The lip seal elastically closes a distal opening of the lumen. The sleeve is also electrically connected to the electrode, which has an external surface and projects distally beyond the lip seal. The electrode may be a ring or tip electrode at the distal end of the electrode assembly. The ring or tip electrode has a sensing or stimulation surface which is operative outwardly in relation to the electrode lead. The electrode may act as either a sensing electrode or a stimulation electrode, depending on its connection to a sensing unit or a stimulation unit of the pacemaker.

In particular, that arrangement of the lip seal within the distal tip or ring electrode affords the particular advantage that the tip or ring electrode can be continued distally of the lip seal so that the sensing or stimulation surface of the electrode can be continued in the distal direction beyond the lip seal and can be of such a design configuration that, even in the case of an electrode lead with passive fixing, by pre-bending of the electrode lead with various angles between the electrode lead tip and the wall of the blood vessel, good contact is always afforded between the sensing or stimulation surface and the wall of the vessel.

Accordingly, in a preferred embodiment, in the region of its distal end, the electrode lead is pre-shaped in such a way that in the unstressed condition it adopts a bend which provides for anchoring of the electrode lead in a blood vessel such as, for example, a lateral vein of a heart, in such a way that the sensing or stimulation surface of the electrode bears against the wall of the blood vessel.

The distal end of the electrode lead is thus formed by the electrode surface which has a central opening through which a guide wire or the like can pass. Arranged in proximal relationship with that electrode surface can be a steroid reservoir which is opened outwardly so that the electrode lead can deliver a steroid.

In addition, in proximal relationship with the electrode surface, the electrode lead has a sheath which is preferably formed from an elastic plastic tube which, for example, comprises silicone. That plastic tube, at least over a part of the length of the electrode lead, has a covering in the form of a polyurethane tube.

At the proximal end of the electrode lead, it preferably carries a connector for connecting the electrode lead to a pacemaker. In that respect, the connector is preferably formed by a standard IS-1 plug.

DETAILED DESCRIPTION OF THE INVENTION

Figure 1:
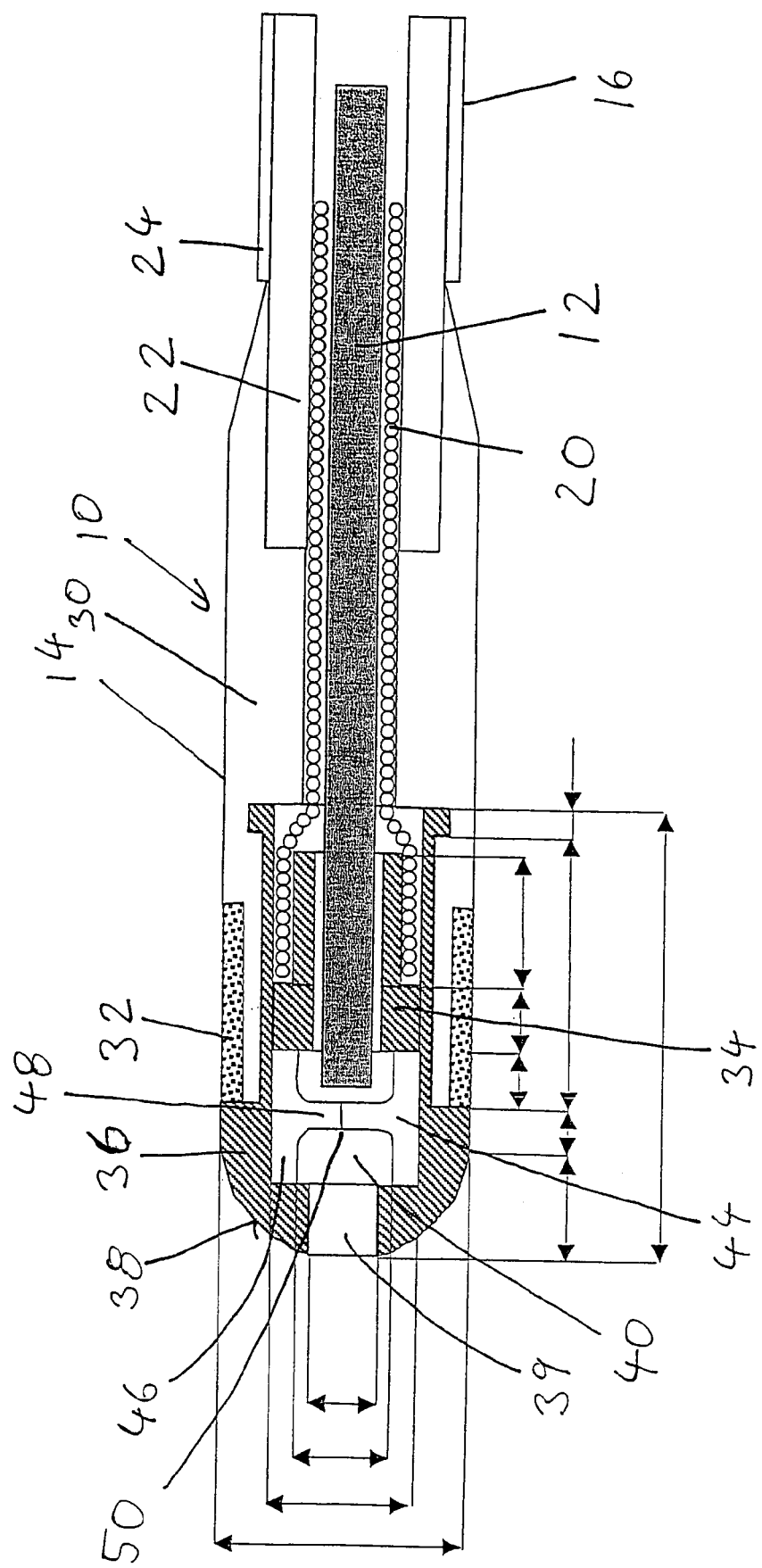
FIG. 1 is a sectional view showing a structure of a distal end of an electrode lead.

The invention will now be described in greater detail hereinafter by means of an embodiment. The embodiment is illustrated in the Figures. FIG. 1 diagrammatically shows the distal end of an electrode lead 10 and a guide wire 12 which is inserted into a lumen of the electrode lead 10. The distal end of the electrode lead 10 includes an electrode head 14 and an electrode line 16 which is connected thereto in proximal relationship.

The electrode line 16 is formed by a helical coil 20 encased by a silicone sheath 22. The silicone sheath 22 carries a covering in the form of a polyurethane tube 24 on its outside. The helical coil is formed by a base wire.

The electrode head 14 includes a plastic body 30, which, at its proximal end, accommodates the distal end of the silicone sheath 22 and sealingly encloses same. Arranged in the region of the distal end of the plastic body 30 on the outside is an optional steroid ring 32 which extends over a length of about 1.5 mm and which is of an outside diameter of about 1.8 mm while the inside diameter is about 1.5 mm. An alternative variant (not shown), with the structure being otherwise unchanged, does not have a steroid ring.

In addition, in the region of its distal end, the plastic body 30 encloses the distal end of the helical coil 20, a sleeve 34 as a crimping sleeve and a proximal part of a tip electrode 36.

The tip electrode 36 extends beyond the distal end of the plastic body 30 and there forms a hemispherical electrode surface 38 with a central through opening 39. The diameter of the through opening 39 is about 0.5 mm.

The proximal part of the tip electrode 36, which is enclosed by the plastic body 30, is connected to a distal sleeve 34. The sleeve 34 is extended into the interior of the enlarged distal end of helical coil 20. The helical coil 20 extends approximately as far as the distal flange of the sleeve 34. The electrode head 14 together with the sleeve 34 encloses a cavity 40 which is delimited in the radial direction by the electrode head 14. The cavity 40 is continued in the distal direction into the through opening 39. In the proximal direction, the cavity is delimited by the distal flange of the sleeve 34. A lip seal 44 of silicone is fitted into the cavity 40. The lip seal 44 has a peripheral wall 46 which bears in sealing relationship against the peripheral wall of the cavity 40, that wall being formed by the tip electrode 36. In addition, the lip seal 40 includes a sealing diaphragm 48 with a central opening 50.

The guide wire 12 can be further advanced beyond the position shown in FIG. 1 in the distal direction of the electrode lead and in so doing pierces the lip seal 40. In that situation the lip seal 40 bears snugly against the guide wire 12 so that the internal lumen of the electrode lead 10 is sealed in relation to the exterior of the electrode lead by the lip seal 44 both in the condition shown in FIG. 1 and also when the guide wire 12 is in the distally advanced position.

Figure 2:
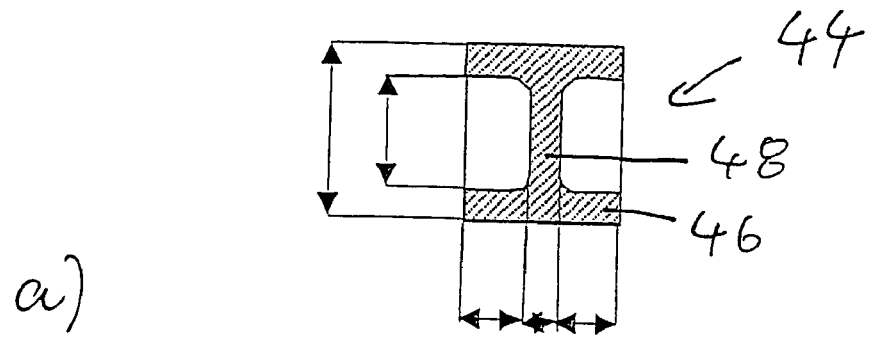
FIGS. 2a through d show alternative configurations of a sealing element for a distal end of an electrode lead as shown in FIG. 1.
Figure 2:
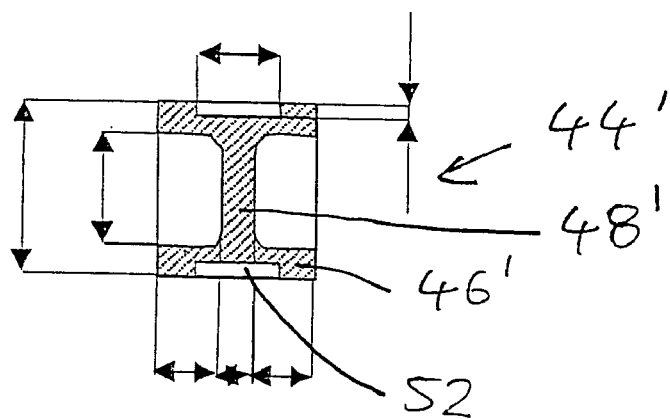
Figure 2:
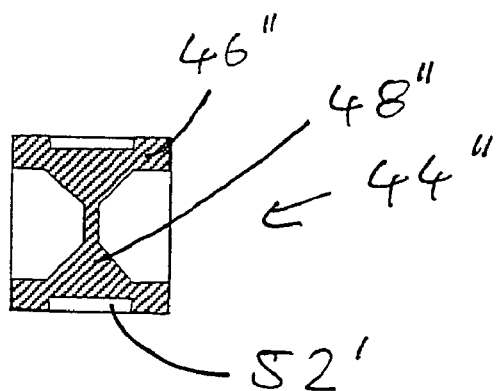
Figure 2:
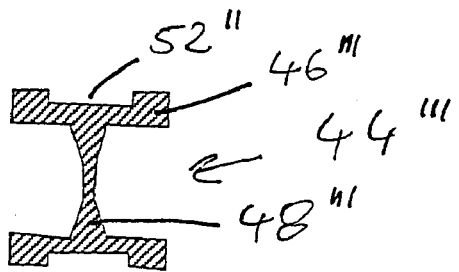

FIGS. 2a through d show a total of four different alternative configurations for lip seals 44, 44', 44" and 44'''. The lip seal 44 shown in FIG. 2a corresponds to the lip seal shown in FIG. 1. The lip seal 44' shown in FIG. 2b differs from that variant in that the peripheral wall 46' has recesses 52 which inter alia permit evasion deflection movement of the sealing diaphragm 48' when the guide wire is inserted. FIG. 2c has a sealing diaphragm 48", the wall thickness of which increases towards the peripheral wall 46". The sealing diaphragm 48" is of a constant wall thickness only in a central region. The lip seal 44''' shown in FIG. 2d is very similar to the lip seal 44' shown in FIG. 2c. It is only the increase in the wall thickness of the sealing diaphragm 48''' that is not quite so pronounced as in the alternative configuration shown in FIG. 2c.

Figure 3:
FIG. 3 shows a proximal end of the electrode lead with connecting plug.

FIG. 3 shows a conventional IS-1 electrode lead plug 60. It is electrically connected to the helical coil 20 of the electrode lead 10 and serves as a connector for connecting the electrode lead 10 to a cardiac pacemaker.

Figure 4:
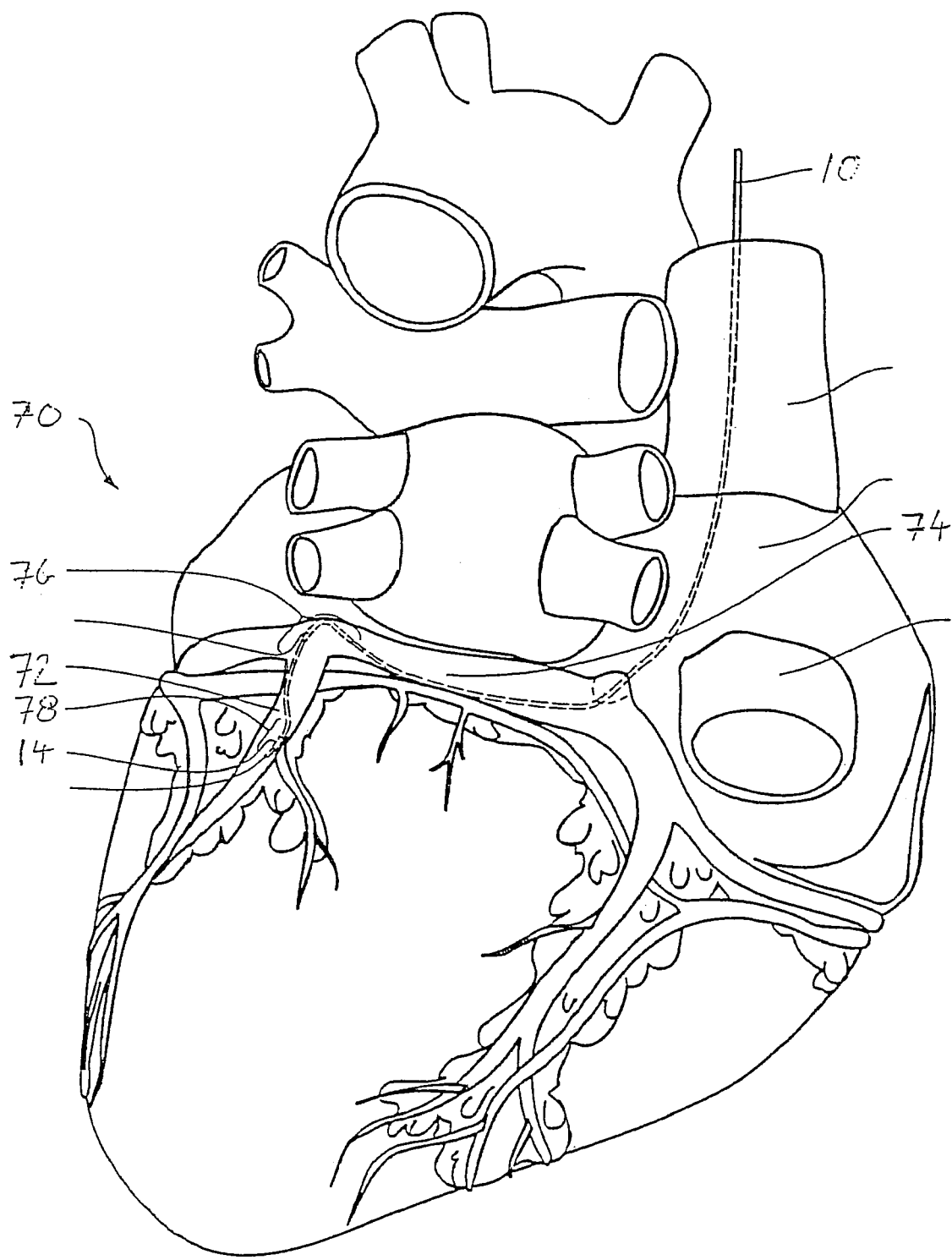
FIG. 4 shows an implanted, pre-bent electrode lead.

FIG. 4 is a view in section through a human heart 70 shows how a pre-bent electrode lead 10 is introduced into a lateral vein 72 of the heart 70, which branches from the coronary sinus 74 of the heart 70. Passive fixing of the electrode lead 10 in the lateral vein is afforded by pre-bending of the electrode lead 10 in the regions 76 and 78. In that way the electrode head 14 bears securely against the vessel wall of the lateral vein 72.

The invention claimed is:

1. An intracardial electrode lead adapted for connection to a cardiac therapy device, comprising:
   a distal end,
   a proximal end, and
   an elongate electrode lead body, which includes a longitudinally extending helical coil having a lumen suitable for containing a guide wire, and a sheath enclosing the helical coil,
   wherein the distal end of the electrode lead carries an electrode, electrically connected to a connector at the proximal end of the electrode lead for communication with a medical device, wherein the electrode has an internal surface and an external surface,
   wherein the distal end of the electrode lead comprises a sleeve having a proximal end and a distal end, which is enclosed by a plurality of distal turns of the helical coil at the sleeve proximal end and contacts a lip seal at the sleeve distal end,
   wherein the lip seal has a peripheral wall which bears in a sealing relationship against the internal surface of the electrode from a distal end of the lip seal to a proximal end of the lip seal, and wherein the lip seal includes a sealing diaphragm with a central opening that elastically closes a distal mouth opening of the lumen and wherein the sealing diaphragm has a thickness that is less than the extent of the lip seal peripheral wall from its distal end to its proximal end, and wherein the sleeve is also electrically connected to the electrode, and wherein the electrode projects distally beyond the lip seal.

2. An electrode lead according to claim 1, wherein the lip seal comprises silicone.

3. An electrode lead according to claim 1, wherein the sheath includes a tube of elastic plastic material.

4. An electrode lead according to claim 3, wherein the sheath comprises silicone.

5. An electrode lead according to claim 3, wherein the tube of elastic plastic material is sheathed by a polyurethane tube over at least part of the length of the electrode lead.

6. An electrode lead according to claim 1, wherein the distal end additionally comprises an outwardly open annular steroid reservoir.

7. An electrode lead according to claim 1, wherein the distal end of the electrode lead has a diameter of about 2.0 mm over the major part of its length.

8. An electrode lead according to claim 1, wherein the distal end of the electrode lead is pre-shaped in such a way that in an unstressed condition, it assumes a bend which provides for anchoring of the electrode lead in a blood vessel in such a way that the surface of the electrode bears against the wall of the blood vessel.

9. An electrode lead according to claim 1, wherein the connection at the proximal end of the electrode lead is a standard IS-1 plug.

10. An electrode lead according to claim 1, wherein the electrode is selected from the group consisting of tip electrodes and ring electrodes.

11. An electrode lead according to claim 1, wherein the electrode is in communication with at least one of a sensing unit of a pacemaker and a stimulation unit of a pacemaker.

12. An electrode lead according to claim 1, wherein the proximal end of the assembly is in communication with a medical device.

13. The electrode lead according to claim 12, wherein the medical device is selected from a cardiac pacemaker, a defibrillator, and a cardioverter.

14. The electrode lead according to claim 1, wherein the peripheral wall of the lip seal contains one or more recesses.

15. The electrode of claim 14, wherein the sealing diaphragm has a constant wall thickness in a central region of the diaphragm and a wall thickness in a peripheral region of the diaphragm that increases from the central region to the peripheral wall.

16. A method of medically treating a patient, the method comprising inserting an electrode lead into a blood vessel of a patient, wherein the electrode lead comprises:
   a distal end,
   a proximal end, and
   an elongate electrode lead body, which includes a longitudinally extending helical coil having a lumen suitable for containing a guide wire, and a sheath enclosing the helical coil,
   wherein the distal end of the electrode lead carries an electrode, electrically connected to a connector at the proximal end of the electrode lead for communication with a medical device, wherein the electrode has an internal surface and an external surface,
   wherein the distal end of the electrode lead comprises a sleeve having a proximal end and a distal end, which is enclosed by a plurality of distal turns of the helical coil at the sleeve proximal end and contacts a lip seal at the sleeve distal end, wherein the lip seal has a peripheral wall which bears in a sealing relationship against the internal surface of the electrode from a distal end of the lip seal to a proximal end of the lip seal, and wherein the lip seal includes a sealing diaphragm with a central opening that elastically closes a distal mouth opening of the lumen and wherein the sealing diaphragm has a thickness that is less than the extent of the lip seal peripheral wall from its distal end to its proximal end, and wherein the sleeve is also electrically connected to the electrode, and wherein the electrode projects distally beyond the lip seal.

17. The method of claim 16, wherein the blood vessel of the patient is a lateral vein of the heart of the patient.

18. The method of claim 16, wherein the electrode lead is secured in the blood vessel by a configuration of the distal end of the assembly wherein the distal end assumes a bent shape in an unstressed condition.

19. The method of claim 16, additionally comprising delivering a pharmaceutical composition to the patient from an outwardly open annual reservoir located in the distal end of electrode lead.

20. The method of claim 16, wherein the electrode is in communication with at least one of a sensing unit of a pacemaker and a stimulation unit of a pacemaker.

* * * * *